(12) United States Patent
Yang et al.

(10) Patent No.: US 9,456,962 B2
(45) Date of Patent: Oct. 4, 2016

(54) TISSUE CONDITIONER FOR DENTAL APPLICATION

(71) Applicant: NATIONAL TAIWAN UNIVERSITY, Taipei (TW)

(72) Inventors: Tsung-Chieh Yang, Taipei (TW); Kuo-Chung Cheng, Taipei (TW); Bor-Shiunn Lee, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/794,173

(22) Filed: Jul. 8, 2015

(65) Prior Publication Data

US 2016/0199265 A1     Jul. 14, 2016

(30) Foreign Application Priority Data

Jan. 13, 2015   (TW) .............................. 104101129 A (51) Int. Cl.
*A61K 6/00*      (2006.01)
(52) U.S. Cl.
CPC .................................. *A61K 6/0026* (2013.01)
(58) Field of Classification Search
CPC .................................................... A61K 6/0026
See application file for complete search history.

(56) References Cited

U.S. PATENT DOCUMENTS

| | | | |
|---|---|---|---|
| 5,136,014 A * | 8/1992 | Figuly | A61K 9/204 528/272 |
| 7,312,256 B2 | 12/2007 | Borja | |
| 7,906,565 B2 * | 3/2011 | Hashiguchi | A61K 6/0026 523/120 |
| 2006/0058415 A1 | 3/2006 | Arthur et al. | |
| 2006/0106128 A1 * | 5/2006 | Borja | A61K 6/0026 523/120 |
| 2007/0043142 A1 | 2/2007 | Dodiuk-Kenig et al. | |

FOREIGN PATENT DOCUMENTS

| | | |
|---|---|---|
| TW | 200621320 | 7/2006 |
| TW | I306405 | 2/2009 |

OTHER PUBLICATIONS

Taiwanese Office Action, dated Nov. 24, 2015, in a counterpart Taiwanese patent application, No. TW104101129.
Nishijima et al., "Cytocompatibility of New Phthalate Ester-free Tissue Conditioners in vitro", Dental Materials Journal, 21(2) pp. 118-132, 2002.

\* cited by examiner

*Primary Examiner* — Michael Pepitone
(74) *Attorney, Agent, or Firm* — Chen Yoshimura LLP (57) ABSTRACT

The present invention provides a tissue conditioner for dental application and comprises a first composition comprising poly ethylmethacrylate (PEMA) and a second composition comprising acetyl tributyl citrate (ATBC), a hyperbranched polyester, and ethanol. The tissue conditioner of the present invention is able to improve the stability of viscoelasticity.

8 Claims, 10 Drawing Sheets

TISSUE CONDITIONER FOR DENTAL APPLICATION

FIELD OF THE INVENTION

The present invention generally relates to a tissue conditioner for dental application, and more particularly, certain embodiments of the invention relate to a tissue conditioner that improves the stability of viscoelasticity.

BACKGROUND OF THE INVENTION

For partially and completely edentulous patients who wear dentures, their oral soft tissues may change after functional and physiological stimuli. The dentures may become loosening due to insufficient adhesion. Clinically, a tissue conditioner is utilized at resin denture base for improving the adhesion of the denture and to reduce discomfort of the oral cavity.

The commercially available tissue conditioner usually comprises two parts, powder and liquid. The powder, without an initiator, is the essential polymer component in the tissue conditioner. The liquid usually comprises a plasticizer and a solvent. Because there are many types of plasticizer, the composition of the liquid is the major difference among different tissue conditioners.

Currently, in clinics, tissue conditioner usually faces a problem of rapid degradation of viscoelasticity, which results in high frequency of replacement. The degradation of viscoelasticity is due to the leaching of the plasticizer and solvent in the tissue conditioner. Therefore, a tissue conditioner which is durable and has stable viscoelasticity is required.

SUMMARY OF THE INVENTION

One aspect of the present invention is to provide a tissue conditioner for dental application, comprising: the first composition comprising poly ethylmethacrylate (PEMA), and a second composition, comprising acetyl tributyl citrate (ATBC), hyperbranched polyester, and ethanol.

BRIEF DESCRIPTION OF THE DRAWINGS

Various objects and advantages of the present invention will be more readily understood from the following detailed description when read in conjunction with the appended drawing, in which.

DESCRIPTION OF EMBODIMENTS OF THE INVENTION

A tissue conditioner of the present invention comprises the first composition and the second composition. The first composition comprises poly ethylmethacrylate (PEMA), which covers PEMA itself as well as a polymer containing PEMA.

In an embodiment of the invention, a molecular weight of the PEMA is not limited to a specific range or value; for example, the number average molecular weight (Mn) of the PEMA may be about $1.0 \times 10^5$ g/mol to $9.5 \times 10^5$ g/mol; for example, $3 \times 10^5$ g/mol, $5 \times 10^5$ g/mol, $8 \times 10^5$ g/mol, $8.5 \times 10^5$ g/mol etc. In an embodiment of the invention, a molecular weight of the PEMA may be but not limited to about $5.5 \times 10^5$ g/mol to $9.0 \times 10^5$ g/mol.

In an embodiment of the invention, the first composition may be in a form of powder. The average diameter of the particles of the first composition may be between 20 μm and 60 μm, for example, 25 μm, 30 μm, 40 μm, 50 μm, 55 μm etc. In a preferred embodiment of the invention, the average diameter of the particles of the first composition may be between 35 μm and 45 μm.

The second composition comprises acetyl tributyl citrate (ATBC), hyperbranched polyester, and ethanol; wherein the acetyl tributyl citrate may be utilized as a plasticizer.

In an embodiment of the invention, in the second composition, the weight ratio of the acetyl tributyl citrate and the hyperbranched polyester may be about 75:25 to 99:1, for example, 80:15, 85:15, 90:10, 95:5, or any other ratio between any two aforesaid ratios. In a preferred embodiment of the invention, the weight ratio of the acetyl tributyl citrate and the hyperbranched polyester may be about 87:13 to 92:8.

In an embodiment of the invention, based on the total weight of the second composition, the ethanol may be about 10 wt % to 15 wt %, for example, 11 wt %, 12 wt %, 13 wt %, 14 wt % etc., or any other values between any two aforesaid values.

The second composition comprises hyperbranched polyester. Here, hyperbranched polyester designates to various types of high molecular polyester with three-dimensional hyperbranched structure. The hyperbranched structure is not similar to conventional line structure and network structure, but is close to a spherical structure. The hyperbranched polyester may be naturally characterized as high surface reactivity, low viscosity, low crystallinity, low glass transition temperature, high solubility, and customized molecular weight.

In the present invention, the hyperbranched polyester can reduce the leaching rate of the plasticizer and maintain the viscoelasticity of the tissue conditioner.

The hyperbranched polyester may be constituted by repeated units, and the quantity of the repeated units is not limited. In an embodiment of the invention, the hyperbranched polyester may be of about 1,000 to 20,000 g/mol in average molecular weight ($M_n$). In an embodiment of the invention, the hyperbranched polyester may be of about 3,500 to 10,000 g/mol in weight-average molecular weight ($M_w$).

In an embodiment of the invention, the hyperbranched polyester may be chosen from dicarboxylic acid, carboxylic acid, and chemical compounds having three or four epoxide functional groups which is derived from a fusion reaction of an epoxy compound, dicarboxylic acid and carboxylic acid in a molar ratio of 1:0.2-2:0.5-5. For example, the dicarboxylic acid may be chosen from ethanedioic acid, adipic acid (AA), sebacic acid (SA) etc.; or, optional aromatic carboxylic acid, such as: 2-(2-carboxyphenyl)benzoic acid, benzene-1,2-dicarboxylic acid, benzene-1,3-dicarboxylic acid, benzene-1,4-dicarboxylic acid etc. The carboxylic acid may be chosen from: heptanoic acid (HA), palmitic acid (PA), oleic acid, lauric acid etc., or, chosen from aromatic acid, such as benzoic acid etc.

The epoxy compound may be chosen from trimethylolpropane triglycidyl ether (TMPTGE), N,N-diglycidyl-4-glycidyloxyaniline (TGAP), tris(2,3-epoxypropyl) isocyanurate, tris(4-hydroxyphenyl)methane triglycidyl ether), 4,4'-methylenebis(N,N-diglycidylaniline) (TGDDM) etc.

In an embodiment of the invention, the hyperbranched polyester may be derived from the reaction of trimethylolpropane triglycidyl ether and adipic acid and heptanoic acid, and may be in the structural formula as follows:

wherein, the symbol of "∼∼" indicates a node for repetition units.

In an embodiment of the invention, the first composition may be in a form of powder; the second composition may be in a form of liquid. When applying clinically, the powder of the first composition and the liquid of the second composition are mixed together to form a gel. The product forms when pseudo cross-links occurs among the polymer chains of the PEMA and the plasticizer.

In an embodiment of the invention, the weight ratio of the first and the second compositions may be 0.5~2:2~0.5, such as 0.5~2:2, 0.5~2:1.5, 0.5~2:1, 0.5~2:0.5, 0.5:0.5~2, 1:0.5~2, 1.5:0.5~2, 2:0.5~2 etc. In a preferred embodiment, the weight ratio of the first and the second compositions may be 1~1.5:0.75~1.25. In another preferred embodiment, the weight ratio of the first composition and the second composition may be 1.2:1.

If needed, the tissue conditioner of the present invention may further comprise an additive agent. The additive agent may comprise retarder, catalyst, antiseptic etc., utilized solely or in a combination. In an embodiment of the invention, the tissue conditioner may further comprise poly methyl methacrylate (PMMA) as the retarder to slow down the leaching rate of the plasticizer.

Here, several embodiments are provided for illustrating the present invention.

Embodiment

Preparation of Hyperbranched Polyester TAH

The hyperbranched polyester in the present embodiment is formed from trimethylolpropane triglycidyl ether, adipic acid, and heptanoic acid, in a molar ratio of 1:0.75:1.5. The adipic acid and heptanoic acid are mixed, catalyst tertiary amine is added, then trimethylolpropane triglycidyl ether is added, refluxed in 120° C. for 2 hours, and then refluxed in 140° C. for 12 hours. A structural formula of the derived hyperbranched polyester TAH may be as follows:

The number average molecular weight (Mn) measured by a gel permeation chromatography (GPC) may be about 1306, and the weight-average molecular weight (Mw) may be about 4245.

Other types of hyperbranched polyester and the monomer are listed in Table 1 as follows.

TABLE 1

| Abbreviation of products of hyperbranched polyester | Monomers |
|---|---|
| TAP | TMPTGE-AA-PA |
| TAH | TMPTGE-AA-HA |
| TSP | TMPTGE-SA-PA |
| TSH | TMPTGE-SA-HA |

Preparation of Tissue Conditioner

1. Powder: PEMA, the number average molecular weight (Mn) of which may be about 850,000 g/mol, and the average diameter of which may be about 35-45 μm.

2. Liquid: a solution formed by acetyl tributyl citrate (ATBC) and aforesaid hyperbranched polyester TAH, solved in 99 wt % ethanol, and then ethanol added therein in a ratio according to Table 2.

Additionally, as a comparison, plasticizers of conventional tissue conditioners may comprise butyl phthalyl butyl glycolate (BPBG), dibutyl phthalate (DBP), benzyl benzoate (BB), and tributyl citrate (TBC), all of which may be utilized for preparation of liquid according to aforesaid steps. Further, aforesaid hyperbranched polyester TAH may be added in some categories of TBC for evaluating the effects of TAH.

TABLE 2

| composition | plasticizer weight percent (wt %) | ethanol (wt %) |
|---|---|---|
| ATBC + TAH | 88% | 12% |
| ATBC + TAH | 87% | 13% |
| TBC + TAH | 88% | 12% |
| TBC + TAH | 87% | 13% |
| ATBC | 91% | 9% |
| ATBC | 90% | 10% |
| TBC | 91% | 9% |
| TBC | 90% | 10% |
| BPBG | 96% | 4% |
| BPBG | 95% | 5% |

TABLE 2-continued

| composition | plasticizer weight percent (wt %) | ethanol (wt %) |
|---|---|---|
| DBP | 96% | 4% |
| DBP | 95% | 5% |
| BB | 99% | 1% |
| BB | 98% | 2% |

3. Preparation of Samples of the Tissue Conditioner:

In room temperature 25° C., aforesaid powder and liquid are mixed in a ratio of 1.2:1.0 (w/w), stirred for 30 seconds, poured into a mold (inner diameter 110 mm×inner height 1.5 mm), and then proceeded for gelation in 37° C. for 30 minutes to form a tissue conditioner. Afterward, the tissue conditioner is cut into samples with a proper size according to the requirement of each testing example (detailed later).

Further, three different tissue conditioners sold in the market are utilized as comparison examples, whose product name and composition are listed in Table 3. Samples used here are made according to the user manual.

TABLE 3

| Product name | Powder | Liquid (wt %) | Ratio of powder/ liquid |
|---|---|---|---|
| SHOFU tissue conditioner II ® | PEMA (Mw: 3.54 × 10⁵ g/mol, ave. diameter: 37 (μm) | 87% DBP 13% EtOH | 1.2 |
| GC Soft-liner ® | PEMA (Mw: 2.34 × 10⁵ g · mol⁻¹, ave. diameter: 50.3 (μm) | 4.3% DBP 14.8% EtOH 80.9% BPBG | 1.22 |
| Densply Lynal ® | PEMA (ave. diameter: 37 (μm) | >90% TBC <1% benzoyl peroxide <10% EtOH | 1.5 |

Testing Examples

Gelation Time

The gelation time of a tissue conditioner is an important factor for clinical application. If the gelation time is too short, doctors may not have sufficient time for operation, and if the gelation time is too long, the time to get cured is namely long. To meet the clinical requirement, a reasonable gelation time may be about 120 seconds to 180 seconds.

In room temperature, the powder and liquid of the tissue conditioner are mixed and stirred for 15 seconds, and then it is ready for measurement via a rheometer. The rheometer is set by 0 s-1000 s time scan range, 0.08% shear deformation, 37° C. temperature, 20 mm diameter plate, 1000 μm gap, and 1 Hz oscillating frequency. The gelation time is defined at time when G' equals to G".

Figure 1:
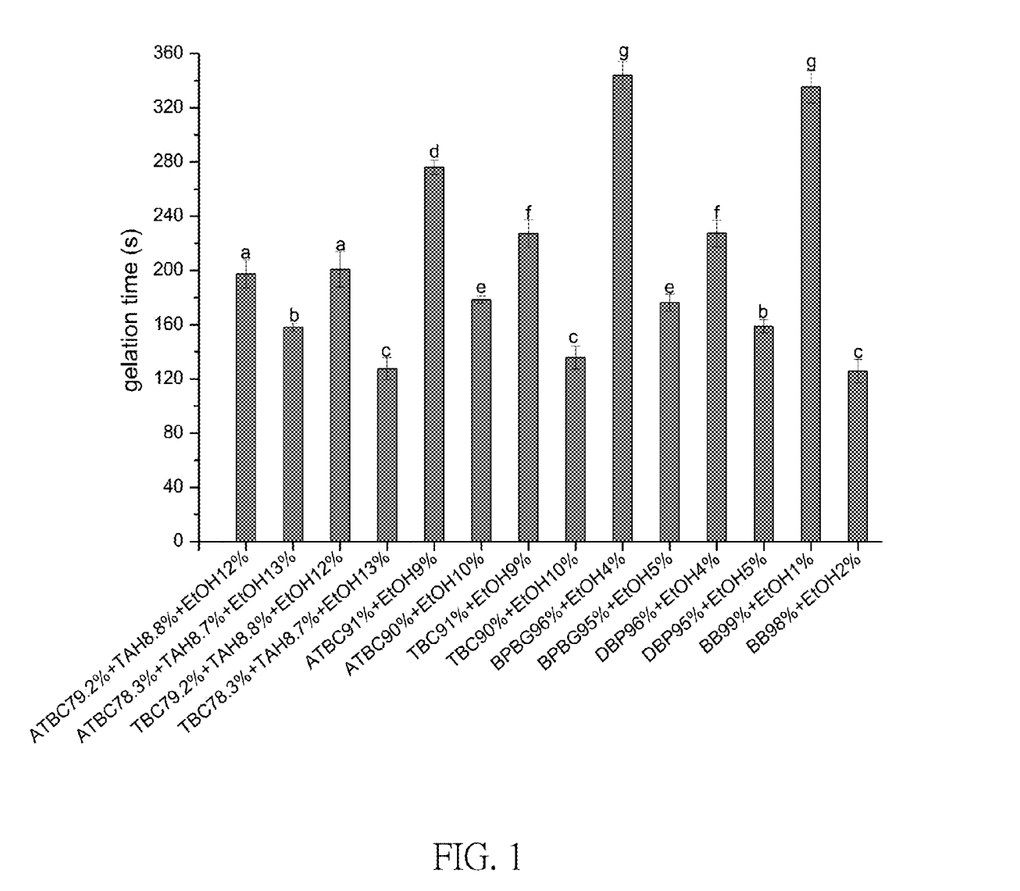
FIG. 1 shows the gelation times of tissue conditioners.
Figure 2A:
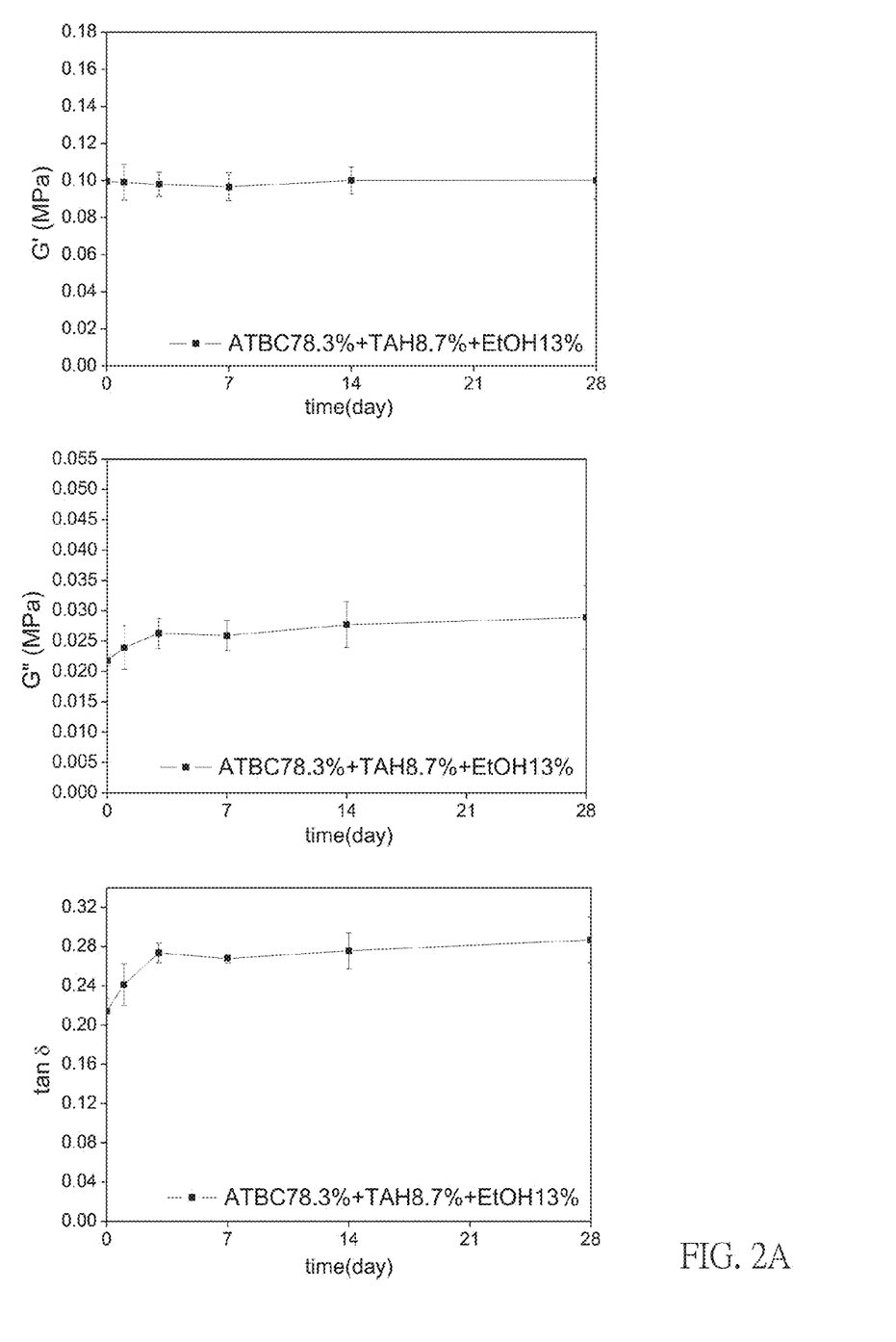
FIGS. 2A to 2F show changes of the viscoelasticity of tissue conditioners for different time periods (1, 3, 7, 14, and 28 d)
Figure 2B:
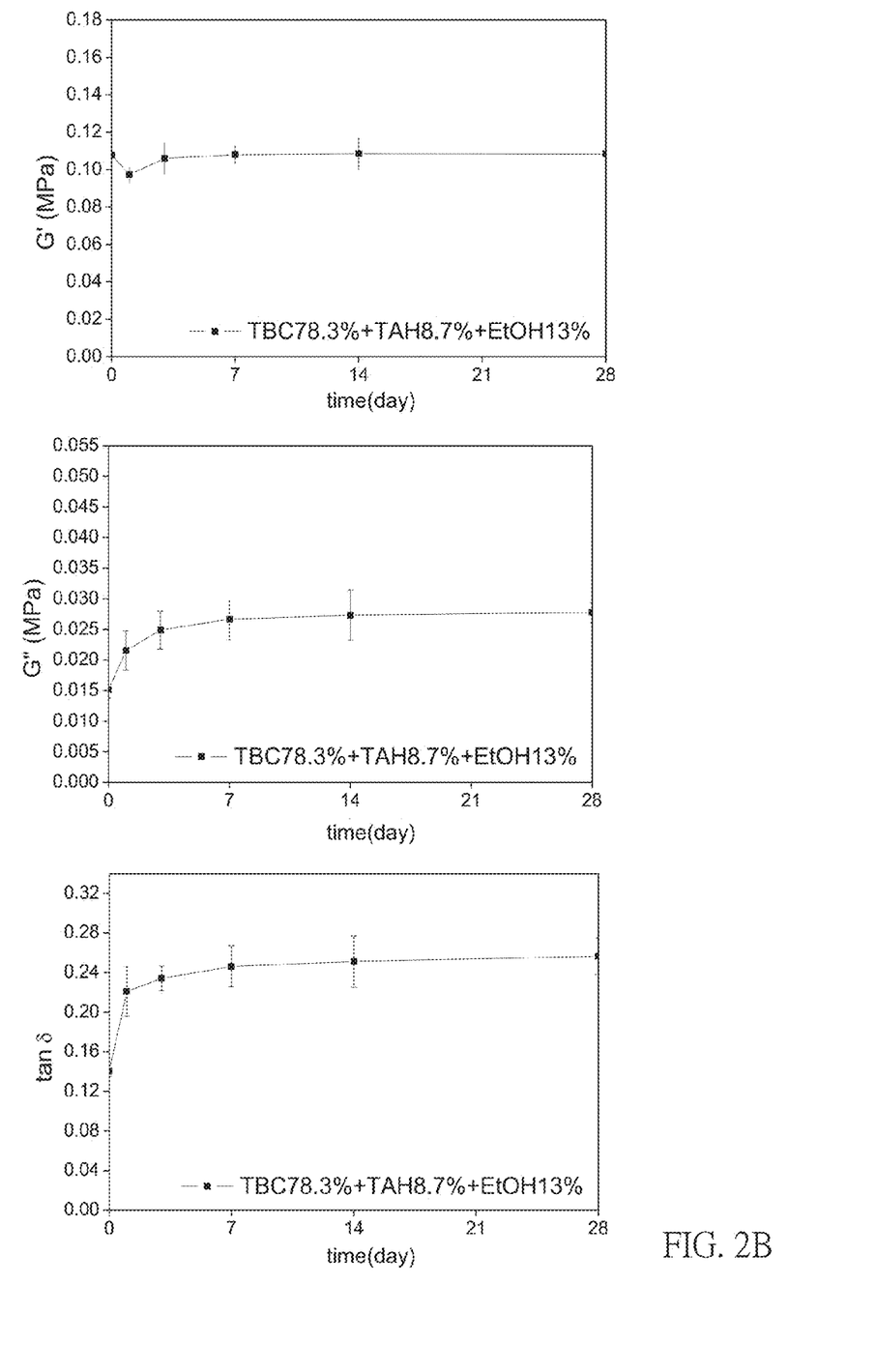
Figure 2C:
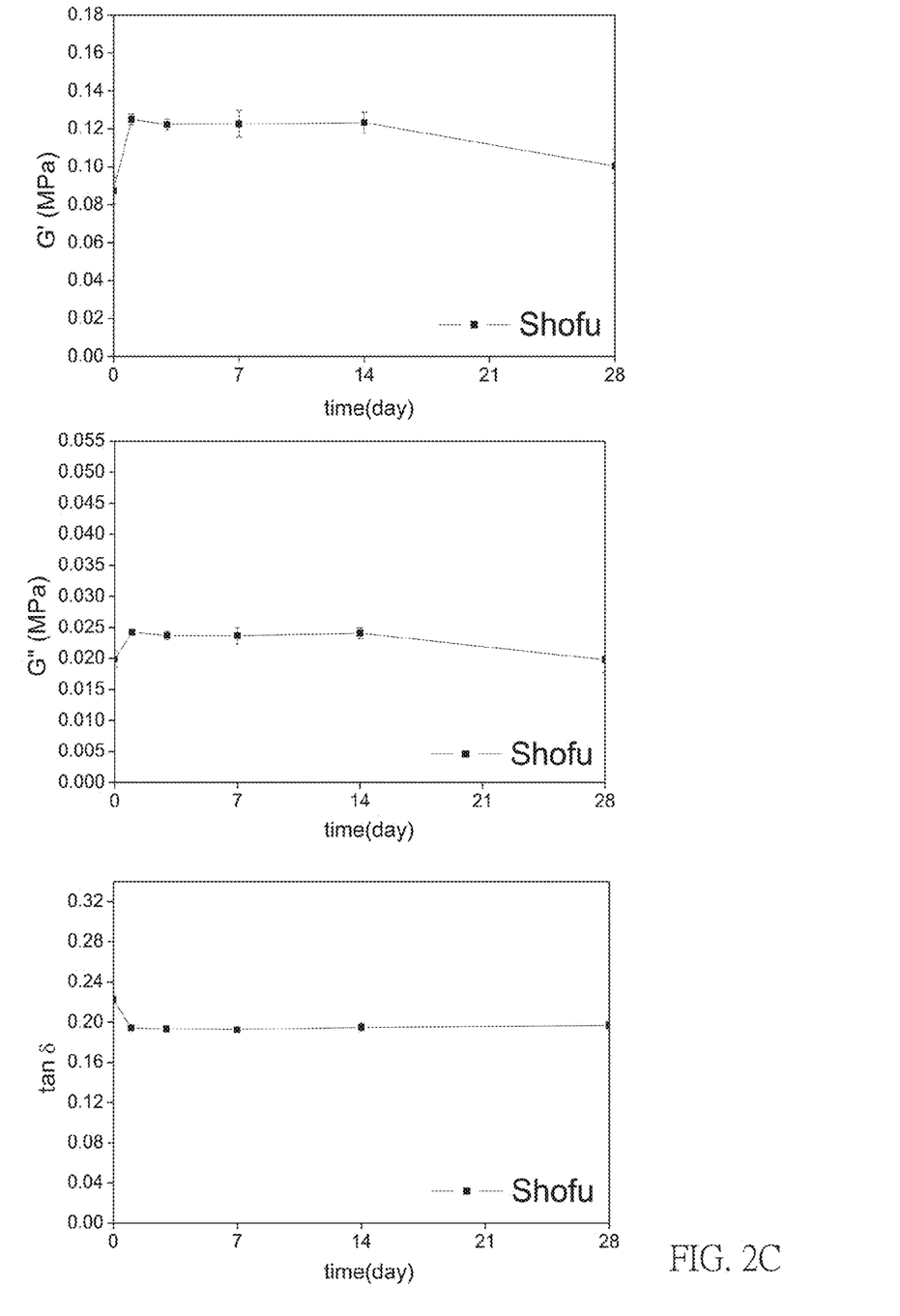
Figure 2D:
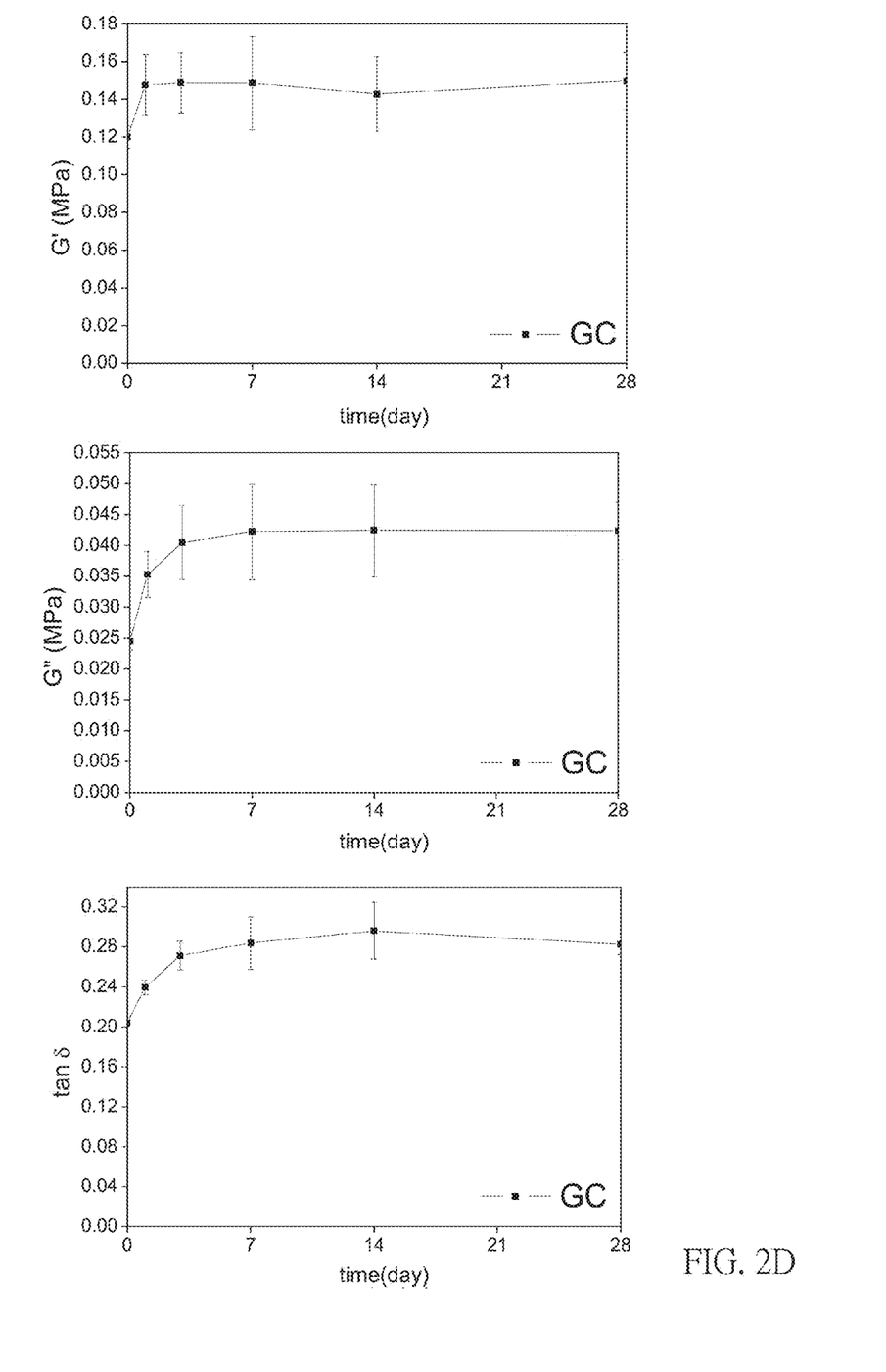
Figure 2E:
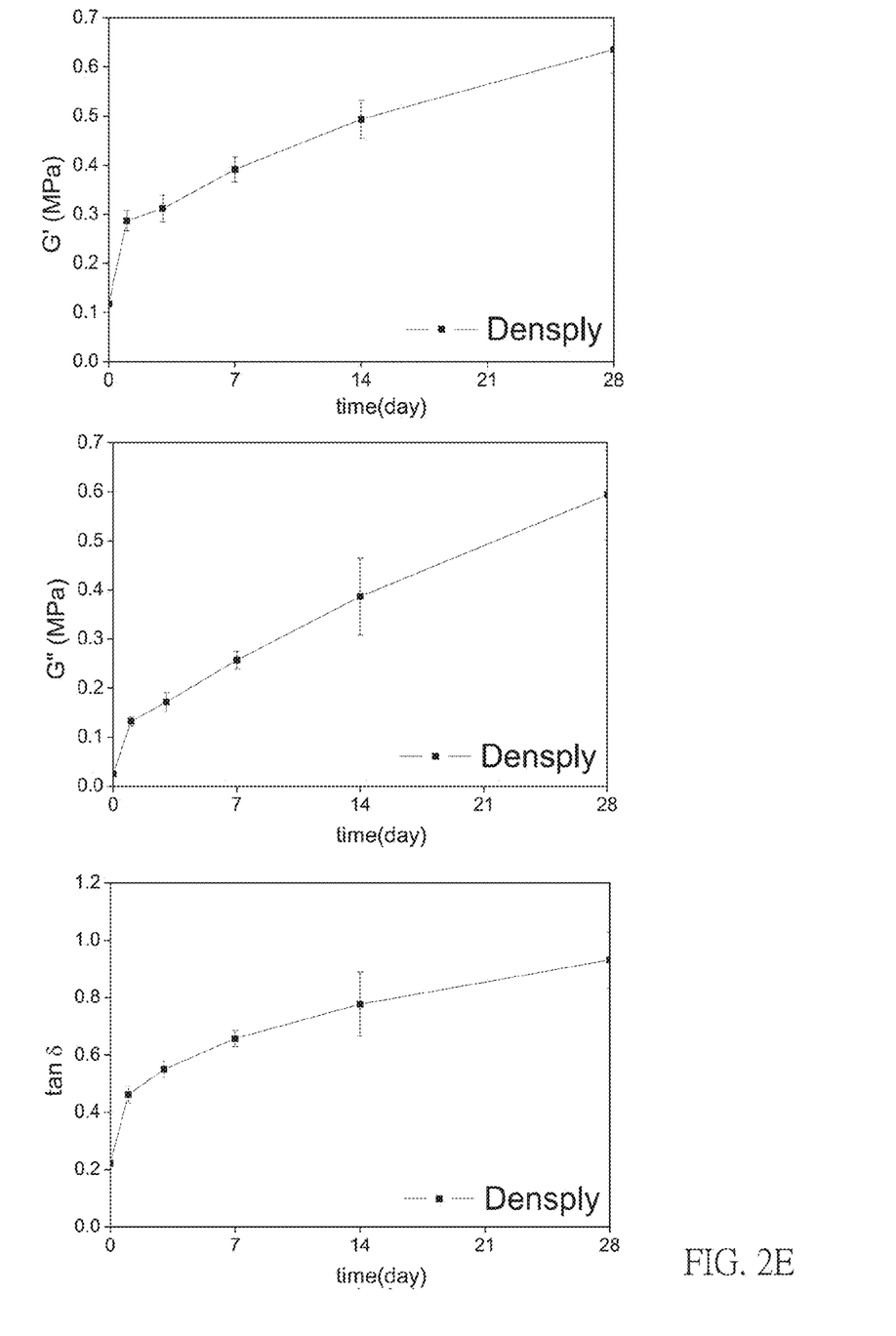
Figure 2F:
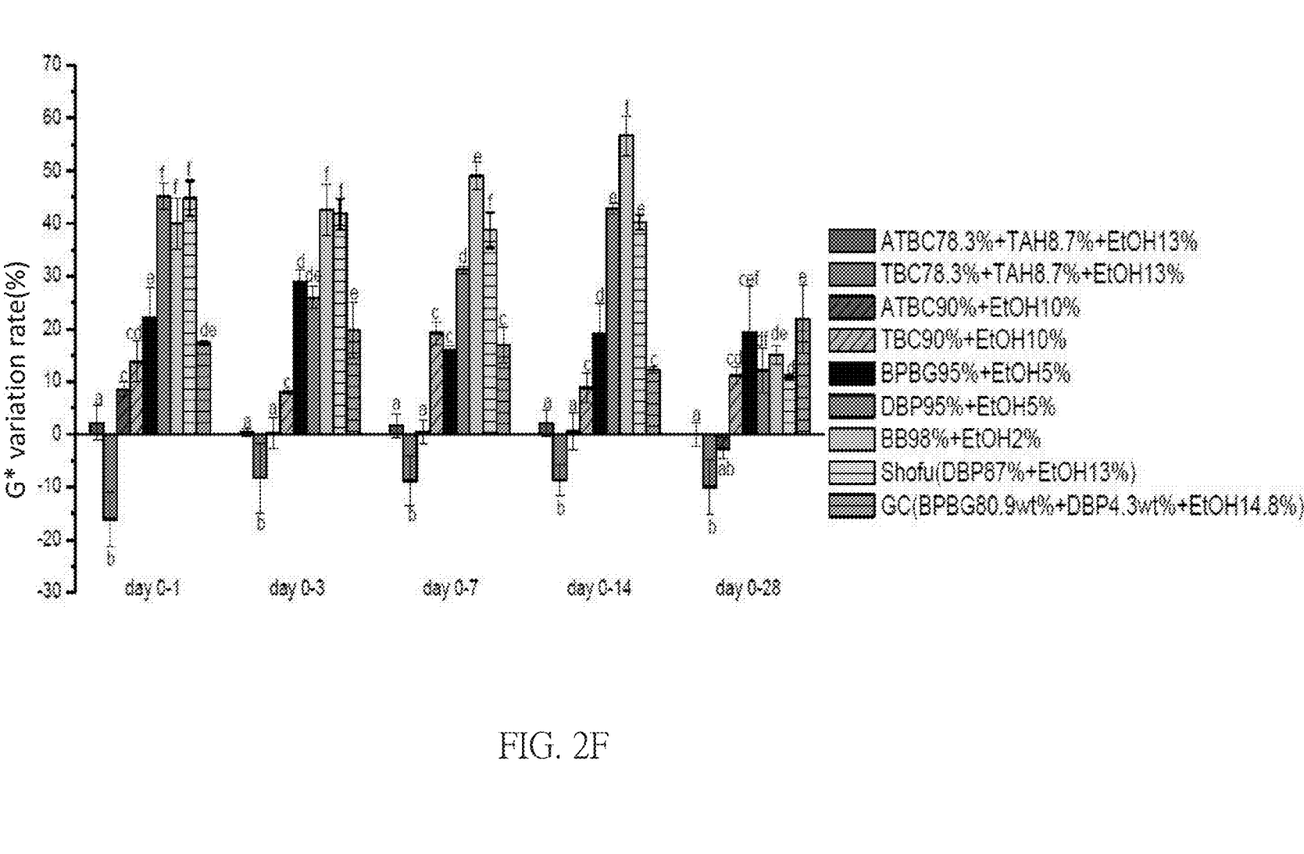

The result is shown in FIG. 1. Gelation times of each group are detailed in Table 4.

TABLE 4

| | Gelation time (sec) | |
|---|---|---|
| | Average | Standard deviation |
| Tissue conditioner in the market | | |
| Shofu | 123.10 | 17.91 |
| GC | 118.13 | 7.89 |
| Composition of liquid | | |
| ATBC79.2% + TAH8.8% + EtOH12% | 197.41 | 10.51 |
| ATBC78.3% + TAH8.7% + EtOH13% | 158.26 | 2.91 |
| TBC79.2% + TAH8.8% + EtOH12% | 200.83 | 12.97 |
| TBC78.3% + TAH8.7% + EtOH13% | 127.66 | 8.19 |
| ATBC91% + EtOH9% | 276.09 | 5.18 |
| ATBC90% + EtOH10% | 178.34 | 2.75 |
| TBC91% + EtOH9% | 227.18 | 10.19 |
| TBC90% + EtOH10% | 135.81 | 8.47 |
| BPBG96% + EtOH4% | 343.90 | 10.13 |
| BPBG95% + EtOH5% | 176.22 | 6.35 |
| DBP96% + EtOH4% | 227.32 | 9.77 |
| DBP95% + EtOH5% | 158.84 | 4.78 |
| BB99% + EtOH1% | 335.38 | 11.96 |
| BB98% + EtOH2% | 125.62 | 8.61 |

Preferably, the gelation time is between 120 to 180 seconds, and the ethanol contained is low, ATBC+TAH+13% ethanol, TBC+TAH+13% ethanol, ATBC+10% ethanol, TBC+10% ethanol, BPBG+5% ethanol, DBP+5% ethanol, BB+2% ethanol.

Test for Stability of Viscoelasticity

Samples are made by cutting the tissue conditioner into disks with 2.5 mm in diameter, 1.5 mm in height. Each group includes five samples (n=5) to test the viscoelasticity through a rheometer (day 0). Then, samples are positioned in 500 mL of de-ionized water, and then placed in an incubator setting up at 37° C. constant temperature for simulation of the oral environment. Then, aforesaid test is repeated in days 1, 3, 7, 14 and 28. The rheometer is set by 0.1-10 Hz frequency scan range, 0.08% shear deformation, 37° C. temperature, 20 mm diameter plate, 1N normal force, storage modulus (G') of samples, loss modulus (G"), tan δ and viscoelasticity variation rate in percentage (G*). A variation rate is calculated according to the formula as follows through G*:

$$\Delta G^{*day0-X}(\%) = G^{*dayX} - G^{*day0}/G^{*day0} \times 100\%.$$

The results are shown in FIGS. 2A to 2F. An observation for the 28 days is that the values of the changing rate of G* of ATBC78.3%+TAH8.7%+EtOH13% group are all less than 2.12%, which is the most stable group and less than that of the two types of tissue conditioners in the market.

Test for Plasticizer Leaching Rate

Samples are made by cutting the tissue conditioner into disks with 3.5 mm in diameter and 1.5 mm in height. Each group includes three samples (n=3). Samples are placed in 50 mL of de-ionized water, and then placed in an incubator setting up at 37° C. constant temperature for simulation of the oral environment. In days 1, 3, 7, 14 and 28, 3 mL of de-ionized water and 6 mL of n-hexane are utilized for extracting the plasticizer, and then UV-visible spectroscopy is utilized for measurement of the plasticizer leaching.

Figure 3A:
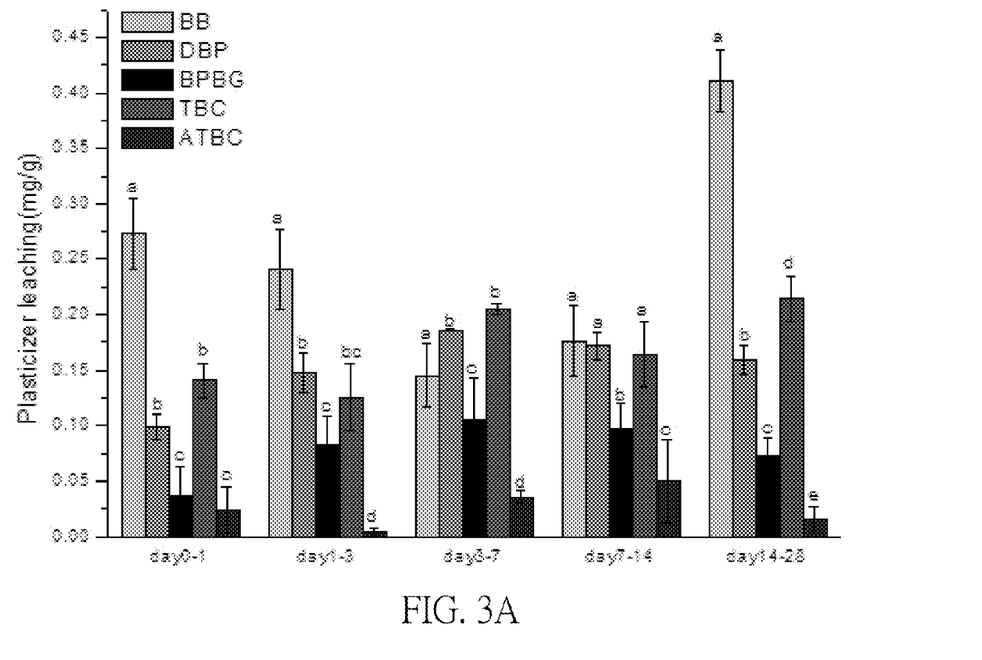
FIG. 3A shows the leaching rate of the plasticizer of tissue conditioners.
Figure 3B:
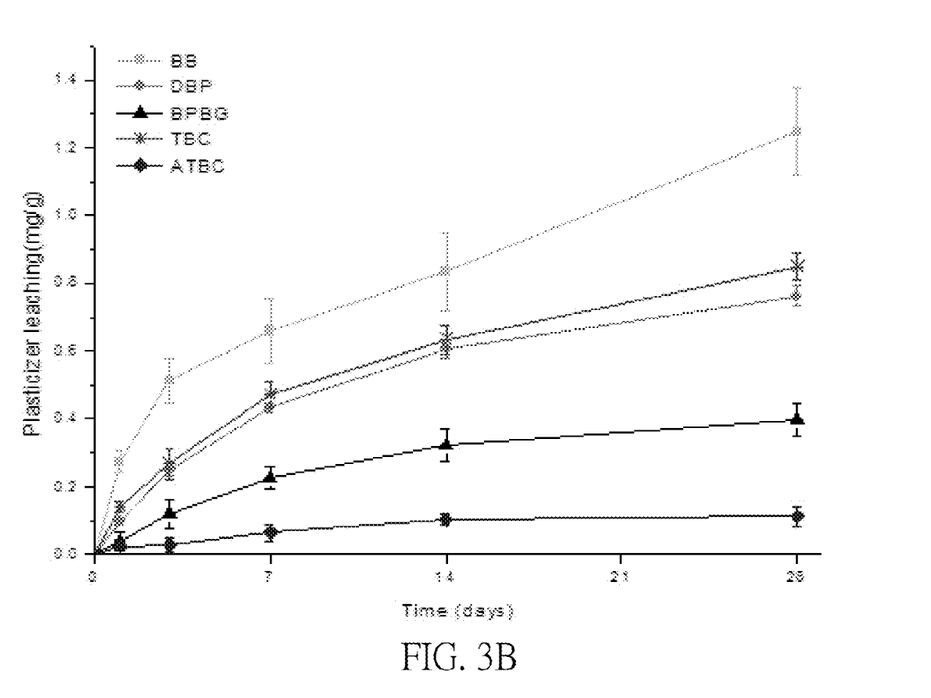
FIG. 3B shows an accumulated leaching rate of the plasticizer of tissue conditioners.

The results are shown in FIGS. 3A and 3B.

FIG. 3A shows the plasticizer leaching rates of all groups, wherein, in days 0-1 and days 14-28, an order of the values of the leaching rate is ATBC<BPBG<DBP<TBC<BB. The leaching amounts of ATBC, BPBG, and DBP reach a constant value in two weeks, while that of BB exhibits higher value in the last two weeks.

FIG. 3B shows an accumulated leaching rate of plasticizers. An order of the value of the leaching rate is ATBC<BPBG<DBP<TBC<BB. The total leaching rate of ATBC in 28 days is about 0.1111±0.0278 mg/g; that of TBC is about 0.8495±0.0424 mg/g; that of BPBG is about 0.3960±0.0477 mg/g; that of DBP is about 0.7629±0.0304 mg/g; that of BB is about 1.2470±0.1292 mg/g.

As shown, compared with conventional plasticizer, the leaching quantity of ATBC from the tissue conditioner is the least.

Test for Surface Hydrophobicity

Deionized water is dropped onto the surface of the sample through a syringe, and then a contact angle between the drop and the sample surface is detected through a static contact angle meter, wherein the number of sample utilized is ten (n=10). In the present testing example, the liquid of the tissue conditioner is categorized into a group of adding ethanol and a group of without ethanol.

As the result shown in Table 5, the greater the contact angle, the stronger the hydrophobicity of the sample surface; on the contrary, the smaller the contact angle, the stronger the hydrophilicity of the sample surface. The contact angle of ATBC is about 89.99±3.94°, the highest among all groups; the contact angle of 90% ATBC+10% TAH is about 62.14±1.65°, which reveals that adding TAH may increase the hydrophilicity. Compared with the results of the stability of viscoelasticity (shown in FIG. 2F), it is readily to conclude that the stability of viscoelasticity of ATBC90%+TAH10% is the highest one among all groups.

TABLE 5

| Group | Liquor without EtOH Average | Liquor without EtOH Standard deviation | Liquor with EtOH Average | Liquor with EtOH Standard deviation |
| --- | --- | --- | --- | --- |
| ATBC90% + TAH10% | 62.14 | 1.65 | 57.31 | 2.36 |
| TBC90% + TAH10% | 60.04 | 1.46 | 39.30 | 1.67 |
| ATBC | 89.99 | 3.94 | 84.78 | 3.18 |
| TBC | 62.99 | 1.28 | 60.81 | 1.29 |
| BPBG | 70.24 | 2.39 | 68.20 | 2.47 |
| DBF | 65.57 | 1.08 | 63.48 | 1.18 |
| BB | 62.67 | 1.75 | 61.17 | 1.84 |
| Shofu | — | — | 64.44 | 1.44 |
| GC | — | — | 60.87 | 1.65 |
| Densply | — | — | 87.11 | 1.52 |

Test for Water Absorption ($W_{sp}$), Solubility ($W_{s1}$), Weight Change ($W_{ch}$)

Disk-shaped samples are formed by cutting the tissue conditioner into disks with 3.5 mm in diameter and 1.5 mm in height. The weight of the samples (M1) is recorded. Then, the samples are placed in 50 mL de-ionized water and then into an incubator setting up at 37° C. constant temperature, the weight is recorded in different days (M), and weight is recorded on the 28$^{th}$ day (M2). After that, the samples are placed in 60° C. temperature until water therein is vaporized, and then the weigh of the samples (M3) is recorded. The number of the sample in each group is 6 (n=6).

Taking M1, M2, M3, M into formulas as follows:

$$W_{sp}(\%)=(M2-M3)/M1\times100\%$$

$$W_{s1}(\%)=(M1-M3)/M1\times100\%$$

$$W_{ch}(\%)=(M-M1)/M1\times100\%$$

Figure 4A:
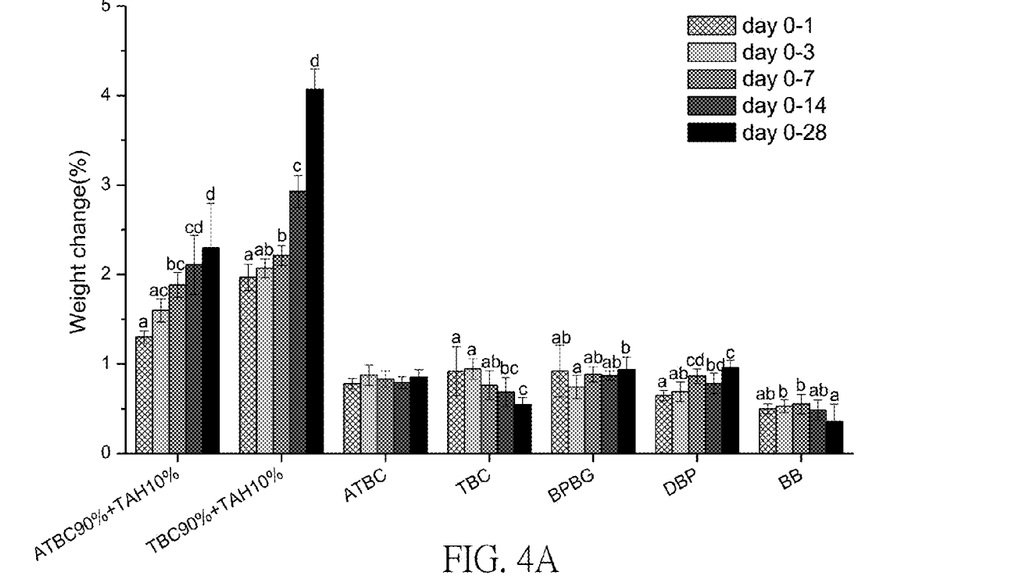
FIG. 4A shows the weight change percentage of tissue conditioners.
Figure 4B:
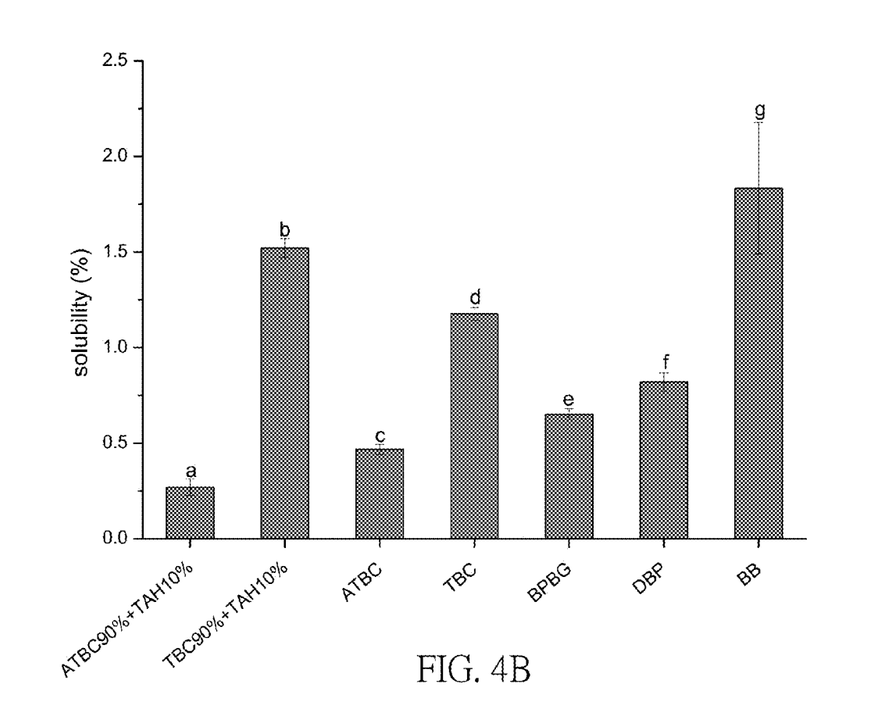
FIG. 4B shows the solubility percentage of tissue conditioners.
Figure 4C:
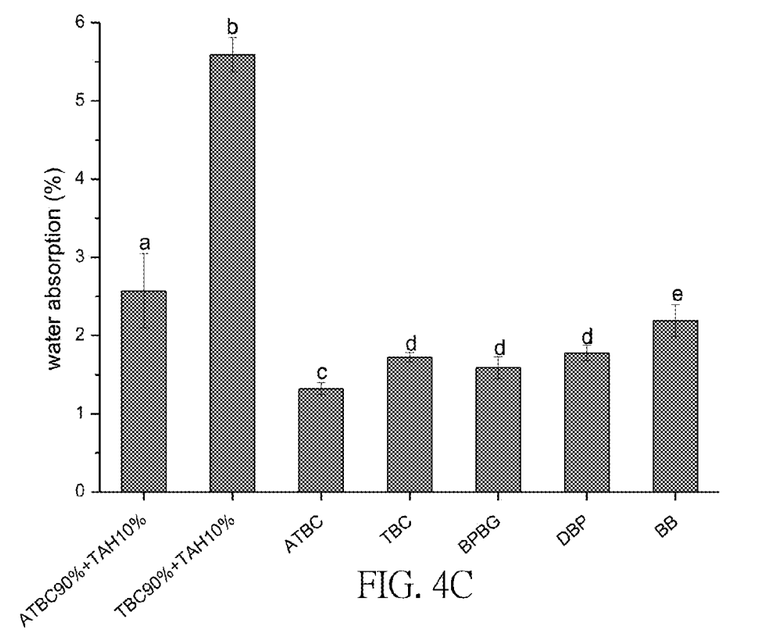
FIG. 4C shows the water absorption percentage of tissue conditioners.

The results are shown in FIGS. 4A to 4C.

FIG. 4A shows the weight change percentage of each group which varies along with time. As shown in FIG. 4A, the weight change of TBC90%+TAH10% is greater than that of ATBC90%+TAH10%, and the weight changes of these two groups are greater than that of the rest groups. FIG. 4B shows solubility percentage of each group. As shown in FIG. 4B, an order of the value of the plasticizer leaching rate is: BB>TBC90%+TAH10%>TBC>DBP>BPBG>ATBC>ATBC90%+TAH10%. FIG. 4C shows a water absorption percentage of each group, and accordingly an order of the water absorption percentage is: TBC90%+TAH10%>ATBC90%+TAH10%>BB>TBC>DBP>BPBG>ATBC. There is no obvious difference among the groups of TBC, BPBG, and DBP.

The less the weight change of the tissue conditioner, the lower the dissolution and water absorption, and the more stable the viscoelasticity. The factors affecting the weight change percentage of the tissue conditioner comprise: leaching of the plasticizer and water absorbed from the environment. In the present 28-day experiment, all weight change percentage are positive, and this represents that the leaching of the plasticizers in all groups is less than the water absorbed from the environment.

Test for Biological Compatibility (MTT Assay)

The tissue conditioner comprising ATBC 78.3 wt %+TAH 8.7 wt %+EtOH 13% is exemplarily utilized for the present testing example. The tissue conditioner is cut into disks with 6 mm in diameter and 1 mm in height. The number of samples in each group is 6 (n=6). The samples are placed in a millipore transwell, and then sterilized with UV light for 24 hours.

Figure 5:
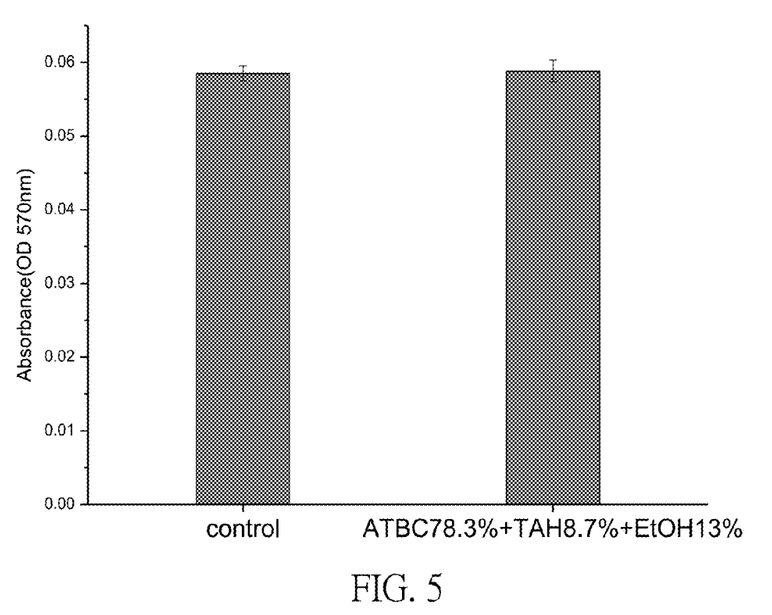
FIG. 5 shows the MTT test result of a tissue conditioner.

Human gingival fibroblasts (HGF) cells are utilized for MTT assay. The number of cells may be about $5\times10^4$/per pore. After cell adhesion is formed, 1 mL of fresh cell culture fluid is added, and then the samples are put in the millipore transwell again for 24 hours culture. Afterwards, MTT assay is performed for detecting the cell activity. Cells without contacting with the tissue conditioner are taken as a control group. As the result shown in FIG. 5, there is no obvious difference between the two groups, and this represents that the tissue conditioner of the present invention may not cause adverse effects in cells.

To sum up, the tissue conditioner of the present invention may present good quality and stability in viscoelasticity, provide a proper gelation time, and without poison on cells. Therefore, the tissue conditioner of the present invention may facilitate application in clinics.

It is to be understood that these embodiments are not meant as limitations of the invention but merely exemplary descriptions of the invention with regard to certain specific embodiments. Indeed, different adaptations may be apparent to those skilled in the art without departing from the scope of the annexed claims. For instance, it is possible to add bus buffers on a specific data bus if it is necessary. Moreover, it is still possible to have a plurality of bus buffers cascaded in series.

What is claimed is:

1. A tissue conditioner for dental application, comprising:
a first composition, comprising poly ethylmethacrylate (PEMA); and
a second composition, comprising acetyl tributyl citrate (ATBC), hyperbranched polyester, and ethanol.

2. The tissue conditioner according to claim 1, wherein a weight ratio of the first composition and second composition is 0.5~2:2~0.5.

3. The tissue conditioner according to claim 1, wherein a weight ratio of the acetyl tributyl citrate and the hyperbranched polyester is 80~99:20~1 in the second composition.

4. The tissue conditioner according to claim 1, wherein the ethanol is 10 wt % to 15 wt %, based on the total weight of the second composition.

5. The tissue conditioner according to claim 1, wherein the hyperbranched polyester is derived from a reaction of monomers of trimethylolpropane triglycidyl ether, adipic acid, and heptanoic acid.

6. The tissue conditioner according to claim 5, wherein a structural formula of the hyperbranched polyester is:

wherein, the symbol " ~~ " indicates a node for repetition units.

7. The tissue conditioner according to claim 1, wherein the first composition is in a form of powder.

8. The tissue conditioner according to claim 7, wherein the first composition comprises poly ethylmethacrylate whose average diameter is 35-45 µm.

* * * * *